(12) United States Patent
Henry et al.

(10) Patent No.: US 11,596,422 B2
(45) Date of Patent: Mar. 7, 2023

(54) ADJUSTABLE BOWEL TREATMENT ARM

(71) Applicant: Hollister Incorporated, Libertyville, IL (US)

(72) Inventors: Jerome A. Henry, Castlebar (IE); William K. Arnold, Gurnee, IL (US); Stephen Collum, Castlebar (IE); Denise Gamblin, Leeds (GB); Ruchi Seth, Libertyville, IL (US); Adam Foley, Swords (IE); Malford E. Cullum, Grayslake, IL (US)

(73) Assignee: Hollister Incorporated, Libertyville, IL (US)

( * ) Notice: Subject to any disclaimer, the term of this patent is extended or adjusted under 35 U.S.C. 154(b) by 964 days.

(21) Appl. No.: 16/347,093

(22) PCT Filed: Oct. 30, 2017

(86) PCT No.: PCT/US2017/058994
§ 371 (c)(1),
(2) Date: May 2, 2019

(87) PCT Pub. No.: WO2018/085196
PCT Pub. Date: May 11, 2018

(65) Prior Publication Data
US 2020/0178988 A1 Jun. 11, 2020

Related U.S. Application Data

(60) Provisional application No. 62/417,132, filed on Nov. 3, 2016.

(51) Int. Cl.
*A61M 3/02* (2006.01)
*A61B 17/22* (2006.01)
(Continued)

(52) U.S. Cl.
CPC ...... *A61B 17/22* (2013.01); *A61B 17/320758* (2013.01); *A61M 3/02* (2013.01); *A61M 3/0233* (2013.01); *A61B 2017/00084* (2013.01); *A61B 2017/00398* (2013.01); *A61B 2017/00424* (2013.01); *A61B 2017/00862* (2013.01); *A61B 2017/00991* (2013.01); *A61B 2017/22037* (2013.01); *A61B 2217/007* (2013.01); *A61M 2209/088* (2013.01)

(58) Field of Classification Search
CPC .... A61M 3/02; A61M 3/0201; A61M 3/0202; A61M 3/0204; A61M 3/0208;
(Continued)

(56) References Cited

U.S. PATENT DOCUMENTS 1,004,103 A 9/1911 Tacey
1,286,083 A 11/1918 Pennington
(Continued)

FOREIGN PATENT DOCUMENTS

CA 2058407 A1 6/1993
CN 104784768 A 7/2015
(Continued)

OTHER PUBLICATIONS

Kayaba, Hiroyuki, Hiroaki Yoshino, Masamichi Itoga, Keiya Kojima and Norihiro Saito. "An Angled Stick Colonic Irrigation Device for the Bowel ManagementPrograms in Patients with Impaired Bowel Function." Journal of General Practice 3:1 (2014).
(Continued)

*Primary Examiner* — Matthew J Lawson
(74) *Attorney, Agent, or Firm* — Cook Alex Ltd.

(57) ABSTRACT

An adjustable bowel treatment arm (110) features a telescoping shaft (112) having a proximal end and a distal end. A handle (118) is secured to the distal end of the telescoping shaft, while a pivot junction (122) positioned at the proximal end of the telescoping shaft. A stem has a proximal end and a distal end, where the distal end of the stem is attached to the pivot junction. A head (124) is attached to the proximal end of the stem.

15 Claims, 11 Drawing Sheets

(51) Int. Cl.
*A61B 17/3207* (2006.01)
*A61B 17/00* (2006.01)

(58) Field of Classification Search
CPC .. A61M 3/0212; A61M 3/0216; A61M 3/022;
A61M 3/0225; A61M 3/0229; A61M
3/0233; A61M 3/0237; A61M 3/0241;
A61M 3/0245; A61M 3/025; A61M
3/0254; A61M 3/0258; A61M 3/0262;
A61M 3/027; A61M 3/0275; A61M
3/0279; A61M 3/0283; A61M 3/0287;
A61M 3/0291; A61M 3/0295; A61B
2017/22037
See application file for complete search history.

(56) References Cited

U.S. PATENT DOCUMENTS

| | | | |
|---|---|---|---|
| 1,710,701 A | 4/1929 | Hertzberg | |
| 1,853,202 A | 4/1932 | Catlin | |
| 3,653,377 A | 4/1972 | Rebold | |
| 3,731,676 A | 5/1973 | Rebold | |
| 3,794,031 A | 2/1974 | Bloom | |
| 3,802,418 A | 4/1974 | Clayton | |
| 3,910,274 A | 10/1975 | Nolan | |
| 4,117,847 A | 10/1978 | Clayton | |
| 4,682,979 A | 7/1987 | Girouard | |
| 4,890,340 A | 1/1990 | Lovitt | |
| 4,943,285 A | 7/1990 | Hawks | |
| 5,097,540 A | 3/1992 | Lovitt | |
| 5,176,630 A | 1/1993 | Shilling et al. | |
| 5,190,519 A | 3/1993 | Mead et al. | |
| 5,405,319 A | 4/1995 | Abell et al. | |
| 5,443,445 A | 8/1995 | Peters et al. | |
| 5,578,017 A | 11/1996 | Aguilar et al. | |
| 5,864,895 A | 2/1999 | Ota et al. | |
| 6,106,506 A | 8/2000 | Abell et al. | |
| 6,125,843 A | 10/2000 | Gold et al. | |
| 6,468,245 B2 | 10/2002 | Alexandersen | |
| 6,569,132 B1 | 5/2003 | Dvärsäter | |
| 6,632,195 B1* | 10/2003 | Smith | A61M 35/25 |
| | | | 604/36 |
| 6,665,888 B1 | 12/2003 | Kwak | |
| 6,751,813 B2 | 6/2004 | Chung | |
| 6,761,702 B2 | 7/2004 | Smith | |
| 6,984,226 B1 | 1/2006 | Abell et al. | |
| 7,147,627 B2 | 12/2006 | Kim et al. | |
| 7,913,329 B2 | 3/2011 | Smith | |
| 7,914,505 B2 | 3/2011 | Moeller-Jensen et al. | |
| 8,079,988 B2 | 12/2011 | Beechie | |
| 8,122,558 B1 | 2/2012 | Maedell et al. | |
| 8,231,589 B2 | 7/2012 | Moeller-Jensen et al. | |
| 8,518,012 B2 | 8/2013 | Smith | |
| 8,568,348 B2 | 10/2013 | Vlodaver et al. | |
| 8,574,206 B2 | 11/2013 | Bjerragaard et al. | |
| 8,579,850 B2 | 11/2013 | Bjerragaard | |
| 8,657,801 B2 | 2/2014 | Nielsen et al. | |
| 8,663,180 B2 | 3/2014 | Tanghoej et al. | |
| 8,868,190 B2 | 10/2014 | Guez | |
| 8,905,981 B2 | 12/2014 | Budig et al. | |
| 9,155,677 B2 | 10/2015 | Lacy | |
| 11,076,977 B2* | 8/2021 | He | A61B 17/22 |
| 2003/0073974 A1 | 4/2003 | Falconer | |
| 2004/0181193 A1 | 9/2004 | Nilsson | |
| 2004/0260152 A1 | 12/2004 | Sant et al. | |
| 2005/0070933 A1 | 3/2005 | Leiboff | |
| 2005/0148954 A1 | 7/2005 | Abell | |
| 2005/0204497 A1 | 9/2005 | Hillenbrand | |
| 2005/0277811 A1 | 12/2005 | Richards et al. | |
| 2006/0009732 A1 | 1/2006 | Hardy | |
| 2006/0025728 A1 | 2/2006 | Leiboff et al. | |
| 2006/0025729 A1 | 2/2006 | Leiboff et al. | |
| 2006/0129135 A1 | 6/2006 | Moeller-Jensen et al. | |
| 2007/0073216 A1 | 3/2007 | McAuliffe et al. | |
| 2008/0065001 A1 | 3/2008 | DiNucci et al. | |
| 2010/0174214 A1 | 7/2010 | Gabbay et al. | |
| 2010/0249752 A1 | 9/2010 | Tanghoej | |
| 2011/0054413 A1* | 3/2011 | Romhild | A61F 5/0093 |
| | | | 604/48 |
| 2011/0144588 A1 | 6/2011 | Taylor et al. | |
| 2011/0282311 A1 | 11/2011 | Nishtala | |
| 2011/0295236 A1 | 12/2011 | Gregory | |
| 2011/0302709 A1 | 12/2011 | Taylor et al. | |
| 2013/0116559 A1* | 5/2013 | Levin | A61M 3/0279 |
| | | | 604/257 |
| 2013/0237920 A1 | 9/2013 | Kokenis | |
| 2013/0245380 A1 | 9/2013 | Vogel | |
| 2013/0245421 A1* | 9/2013 | Andrus | A61B 5/062 |
| | | | 600/409 |
| 2013/0331781 A1 | 12/2013 | Andreen | |
| 2014/0005602 A1 | 1/2014 | Andreen et al. | |
| 2014/0155864 A1 | 6/2014 | Andreen | |
| 2014/0276631 A1 | 9/2014 | Gilman | |
| 2014/0358126 A1 | 12/2014 | Göbel | |
| 2016/0339166 A1* | 11/2016 | Adam | A61M 3/0262 |
| 2018/0043087 A1* | 2/2018 | Foley | A61M 3/022 |
| 2021/0283325 A1* | 9/2021 | Henry | A61M 3/0262 |

FOREIGN PATENT DOCUMENTS

| | | |
|---|---|---|
| DE | 4427067 A1 | 2/1995 |
| EP | 1051984 A2 | 11/2000 |
| EP | 1743616 A1 | 1/2007 |
| EP | 1752177 A1 | 2/2007 |
| EP | 1946785 A1 | 7/2008 |
| EP | 1977778 A1 | 10/2008 |
| EP | 2027832 A2 | 2/2009 |
| EP | 2452706 A2 | 5/2012 |
| EP | 2468326 A1 | 6/2012 |
| EP | 2005981 B1 | 9/2012 |
| EP | 2158926 B1 | 5/2013 |
| EP | 2671601 | 12/2013 |
| EP | 2703019 A1 | 3/2014 |
| GB | 2496900 A | 5/2013 |
| WO | WO1987001596 | 3/1987 |
| WO | 9420059 | 9/1994 |
| WO | WO9625188 A1 | 8/1996 |
| WO | WO9631250 A1 | 10/1996 |
| WO | WO9715335 A1 | 5/1997 |
| WO | WO9749441 A1 | 12/1997 |
| WO | WO9820722 A1 | 5/1998 |
| WO | WO9959656 A1 | 11/1999 |
| WO | WO0149345 A1 | 7/2001 |
| WO | WO0207668 A1 | 1/2002 |
| WO | WO200213887 A1 | 2/2002 |
| WO | WO2074363 A2 | 9/2002 |
| WO | WO03030967 A1 | 4/2003 |
| WO | WO03030968 A1 | 4/2003 |
| WO | WO2004060259 A2 | 7/2004 |
| WO | WO2004112712 A2 | 12/2004 |
| WO | WO2006010556 A1 | 2/2006 |
| WO | WO2006024205 A1 | 3/2006 |
| WO | WO2006135934 A2 | 12/2006 |
| WO | WO2007103995 A2 | 9/2007 |
| WO | WO2008048856 A2 | 4/2008 |
| WO | WO2008058160 A2 | 5/2008 |
| WO | WO2009015152 A1 | 1/2009 |
| WO | WO2009128109 A1 | 10/2009 |
| WO | WO2009144028 A1 | 12/2009 |
| WO | WO2009153973 A1 | 12/2009 |
| WO | WO2010047501 A2 | 4/2010 |
| WO | WO2010077980 A1 | 7/2010 |
| WO | WO2010115430 A1 | 10/2010 |
| WO | WO2010126586 A1 | 11/2010 |
| WO | 2011018092 A1 | 2/2011 |
| WO | WO2011012323 A1 | 2/2011 |
| WO | WO2011075581 A1 | 6/2011 |
| WO | WO2011105644 A1 | 9/2011 |
| WO | WO2011139498 | 11/2011 |
| WO | 2012116816 A1 | 9/2012 |
| WO | WO12120456 | 9/2012 |
| WO | WO2012164559 | 12/2012 |
| WO | WO2013026564 A1 | 2/2013 |
| WO | WO2013026565 A1 | 2/2013 |

(56) References Cited

FOREIGN PATENT DOCUMENTS

| WO | WO2013076446 A1 | 5/2013 |
|----|-----------------|--------|
| WO | WO2013090778 A1 | 6/2013 |
| WO | WO2013163364 | 10/2013 |
| WO | WO2013182593 | 12/2013 |
| WO | WO2013184158 A1 | 12/2013 |
| WO | WO2014064414 A1 | 5/2014 |
| WO | WO2014089278 A1 | 6/2014 |
| WO | 2015031851 A2 | 3/2015 |
| WO | WO2015117141 | 8/2015 |
| WO | 2016007533 A1 | 1/2016 |
| WO | 2016007536 A1 | 1/2016 |

OTHER PUBLICATIONS

International Search Report and Written Opinion of the ISA for PCT Application No. PCT/US2017/058994, dated May 11, 2018, 14 pages.
www.atcmedical.com Sammons Preston Royal Grip™ Suppository Inserter & Digital Bowel Stimulator, Nontoxic, Molded Plastic Handle by Patterson Medical https://www.atcmedical.com/Aids_To_Daily_Living/Aids-_Miscellaneous/Sammons Preston Royal Grip Suppository Inserter Digital Bowel Stimulator Nontoxic Molded Plastic Handle/SD6403/product.aspx?utm_source=nextag&utm_medium=cse&utm_, pp. 1-2, available as early as Jan. 15, 2016.
www.exmed.net Therafin Digi-Sert—E-Z Reach Bowel Management Tool/Stimulator https://www.exmed.net/p-2233-therafin-digi-sert-e-z-reach-bowel-management-toolstimulator.aspx?defaultvariantid=21425&utm_source=nextag&utm_medium=cse&utm_term=the30511each, pp. 1-4, available as early as Jan. 15, 2016.
http://www.ebay.com/itm/Sure-Grip-Suppository-Inserter-/231514642734?var=&hash=item35e759192e:m:m7-KiTiL0OBI4I3FqSBeRPiA, pp. 1-4, available as early as Jan. 15, 2016.
http://www.ebay.com/itm/Rectally-vaginal-gastrointestinal-tract-SZHKT4-Dunes-Kremlin-tablet-/131527219972?hash=item1e9fa21b04:g:MC8AAOSw3xJVbMEI, pp. 1-3, available as early as Jan. 15, 2016.
https://www.pricefalls.com/product/maddak-anus-stimulatoranus-stimulatoreachh725120000/75172197? utm_source=Nextag&utm_medium=cpa&utm_term=&utm_content=&utm_campaign=, pp. 1-2, available as early as Jan. 15, 2016.

* cited by examiner

FIG. 13

ADJUSTABLE BOWEL TREATMENT ARM

CROSS-REFERENCE TO RELATED APPLICATIONS

The present application is the U.S. National Stage of PCT International Patent Application No. PCT/US2017/058994, filed Oct. 30, 2017, which claims the benefit of and priority to U.S. Provisional Application No. 62/417,132, filed Nov. 3, 2016, the contents of both of which are hereby incorporated herein by reference.

FIELD OF THE DISCLOSURE

The present disclosure relates generally to bowel management devices and, in particular, to an adjustable bowel treatment arm.

BACKGROUND

Many individuals suffering from spinal cord injuries or other medical conditions (such as cauda equina syndrome, multiple sclerosis, spina bifida and chronic constipation) require bowel management programs or treatments. Various options are available and include pharmacological (laxatives such as those taken orally or by suppository), digital stimulation, diet control and others. The airy is to provide the user with a regular bowel management routine without constipation or fecal incontinence. The issues of independence, dignity, dexterity and ease of use are important needs to be addressed by a bowel management program and the associated systems and devices.

In a number of bowel management programs, the user must access the rectum using his or her gloved finger(s). For example, the user may need to manually stimulate the anus and rectum to evacuate stools. The user may also need to digitally remove a stool from the rectum using his or her fingers. An irrigation device, suppository or other object may also need to be inserted into the rectum by the user. Even when other bowel management treatments are used, the user may need to use a gloved finger to check for the presence of stool before and/or after the treatment.

While devices that assist patients in digital bowel stimulation and/or the insertion of irrigation heads, suppositories and the like into the rectum exist, they include a non-adjustable shaft with a handle at one end and a holder or other head or tool at the opposite end. A device that more readily and conveniently accommodates the limited dexterity of some users is desired.

SUMMARY

There are several aspects of the present subject matter which may be embodied separately or together in the devices and systems described and claimed below. These aspects may be employed alone or in combination with other aspects of the subject matter described herein, and the description of these aspects together is not intended to preclude the use of these aspects separately or the claiming of such aspects separately or in different combinations as set forth in the claims appended hereto.

In one aspect, an adjustable bowel treatment arm includes a telescoping shaft having a proximal end and a distal end. A handle is secured to the distal end of the telescoping shaft. A pivot junction is positioned at the proximal end of the telescoping shaft. A stem has a proximal end and a distal end and the distal end of the stem is attached to the pivot junction. A head is attached to the proximal end of the stem.

In another aspect, a method is disclosed for inserting a head into a rectum and includes attaching the head to a pivot junction of an arm having a telescoping shaft with a distal end and a proximal end, where the pivot junction is positioned at the proximal end of the telescoping shaft, selecting an angle between the head and the telescoping shaft by manipulating the pivot junction, selecting a length of the telescoping shaft by sliding an inner rod of the telescoping shaft within an outer rod of the telescoping shaft and grasping a handle positioned at the distal end of the telescoping shaft.

DETAILED DESCRIPTION OF EMBODIMENTS

Figure 1:
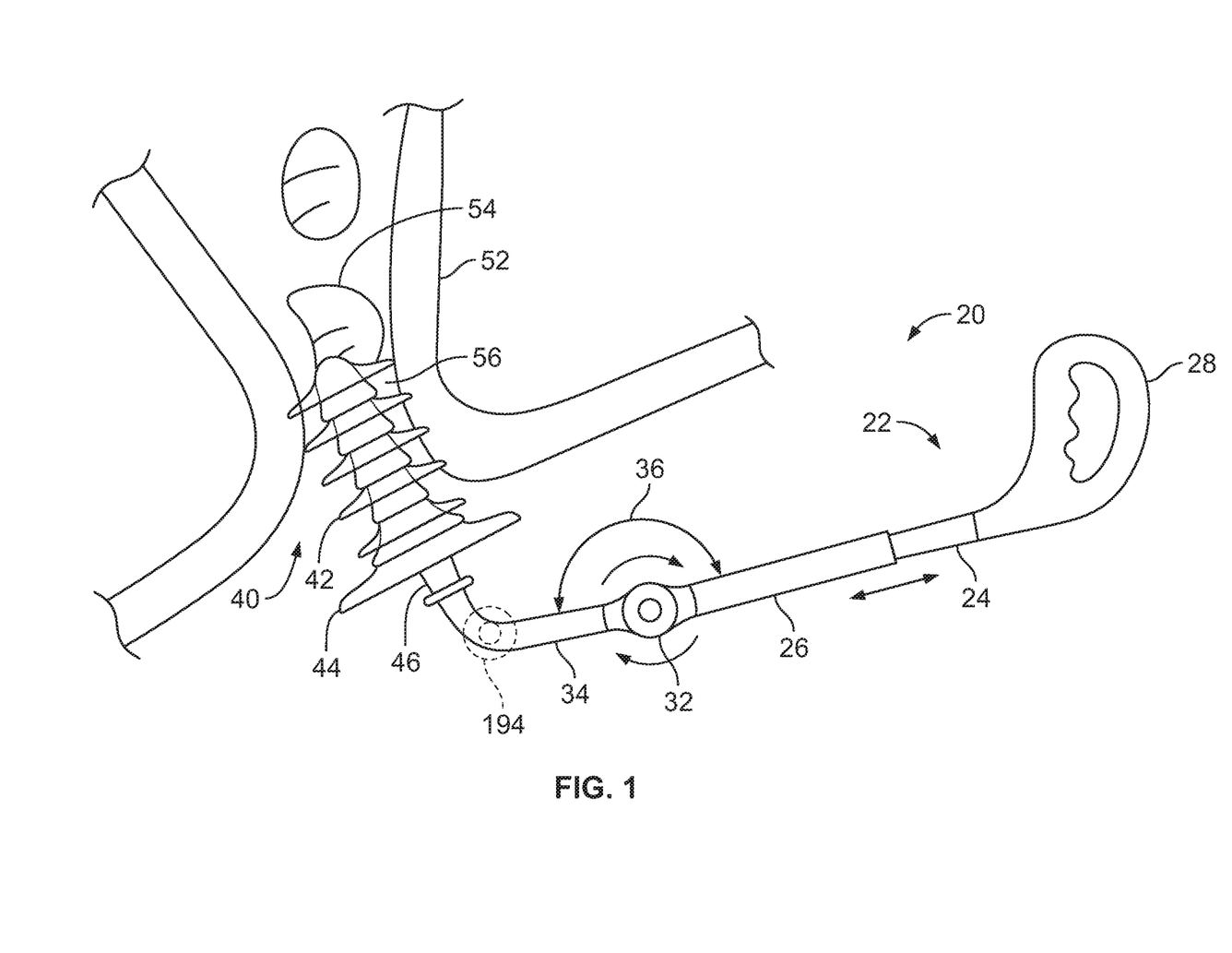
FIG. 1 is a diagrammatic section illustrating insertion of a stool removal head using a first embodiment of the adjustable bowel treatment arm of the disclosure.

An adjustable bowel treatment arm in a first embodiment of the present disclosure is indicated in general at 20 in FIG. 1. The adjustable bowel treatment arm features a telescoping shaft, indicated in general at 22, that includes an inner rod 24 and an outer rod 26. The outer rod 26 features a bore that receives the inner rod 24 in a sliding fashion, but with friction between the outer surface of the inner rod 24 and the inner surface of the outer rod 26 so that the selected length is retained. As a result, the length of the telescoping shaft 22 is adjustable. In other embodiments, the selected length of the telescoping shaft may be retained by other mechanisms known in the art including, but not limited to, a spring pin or locking button, a locking collar, a compression fitting or clamp or a flip clamp. Furthermore, in alternative embodiments, the rod 24 could be the outer rod and the rod 26 could be the inner rod.

A D-shaped handle 28 is attached to the distal end of the inner rod 24 and is ergonomically designed to aid the user in inserting a head or attachment positioned on the proximal end of the device into the rectum when the user is on a toilet or lying in a bed.

The terms "distal" and "proximal" are used throughout this disclosure. When used in the context of the arm, telescoping shaft or stem, the term "proximal" is used to refer to that end or portion of the arm, shaft or stem that, during use, is closer in proximity to the head or tool that is inserted into the user's body and/or initially enters the user's body upon insertion. The term "distal" is used to refer to an end or portion of the arm, shaft or stem that is opposite the proximal end or portion and is typically further away from the user's body and closer to the user's hand when in use.

A pivot junction, indicated in general at 32, is positioned at the proximal end of outer rod 26. An elbow-shaped stem 34 is connected by its distal end to the pivot junction 32 so that the angle of an axis of the stem with respect to the longitudinal axis of the telescoping shaft, indicated at 36 in FIG. 1, is adjustable. As will be explained in greater detail below, a stool removal tool or head, indicated in general at 40, is removably or permanently attached to the proximal end of the stem 34. In the illustrated embodiment, the head is removably attached.

The inner rod 24 may also be twisted about the longitudinal axis of the telescoping shaft 22 with respect to the outer rod 26 so that the roll angle of the handle, about the longitudinal axis of the shaft 22 and with respect to stool removal head 40, or other interchangeable head, may also be adjusted. The friction between the outer surface of the inner rod 24 and the inner surface of the outer rod 26 also retains the selected handle orientation.

Figure 2A:
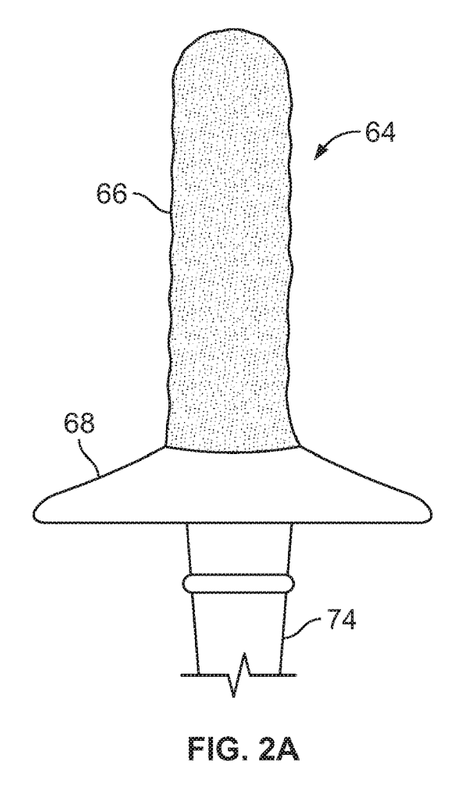
FIGS. 2A-2C illustrate an interchangeable stool checker head, a stool removal head and an irrigator head, respectively, for the adjustable bowel treatment arm of FIG. 1.
Figure 2B:
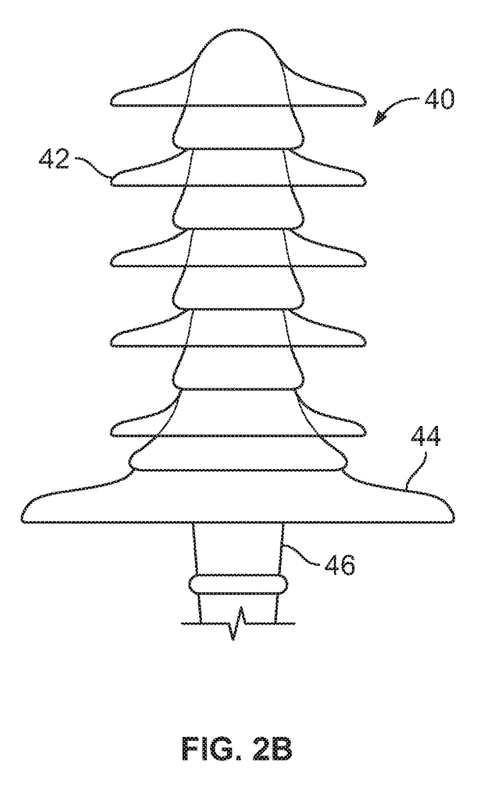

As illustrated in FIGS. 1 and 2B, the proximal end of the bowel treatment arm may be provided with a stool removal head 40. The stool removal head 40 includes a number of concentric, circular fins 42, a circular or disc-shaped shield 44 and a cylindrical or tubular base 46. The stool removal head 40 is preferably molded from a high durometer (as an example only, >50 A) silicone-like resilient material so that it is atraumatic to the anal sphincter and rectum. Alternative resilient materials, such as rubber and plastic, may also be used.

In use, with reference to FIG. 1, a user, after the length of the shaft 22, the angle 36 and the roll angle or orientation of the handle about the longitudinal axis of the shaft 22 is adjusted, grasps the handle 28, positions the shaft 22 between his or her legs, under the legs from the side or otherwise approaches from the side, and positions the stool removal head 40 at the anus. If the user is sitting on a toilet, the shaft 22 may be rested on the toilet seat or rim of the toilet in a lever arrangement. The user then manipulates the arm to insert the stool removal head into his or her rectum.

As illustrated in FIG. 1, the concentric, circular fins 42 have a tapered profile that facilitates circumferential deflection or collapse during insertion into the user's rectum 52. As a result, once inserted into the rectum, the circumferential edges of the fins 42 gently engage the rectum wall. Stool 54 is collected within the annular spaces 56 between the fins and held in place by the fins as the head 40 is withdrawn from the user's rectum.

Figure 3:
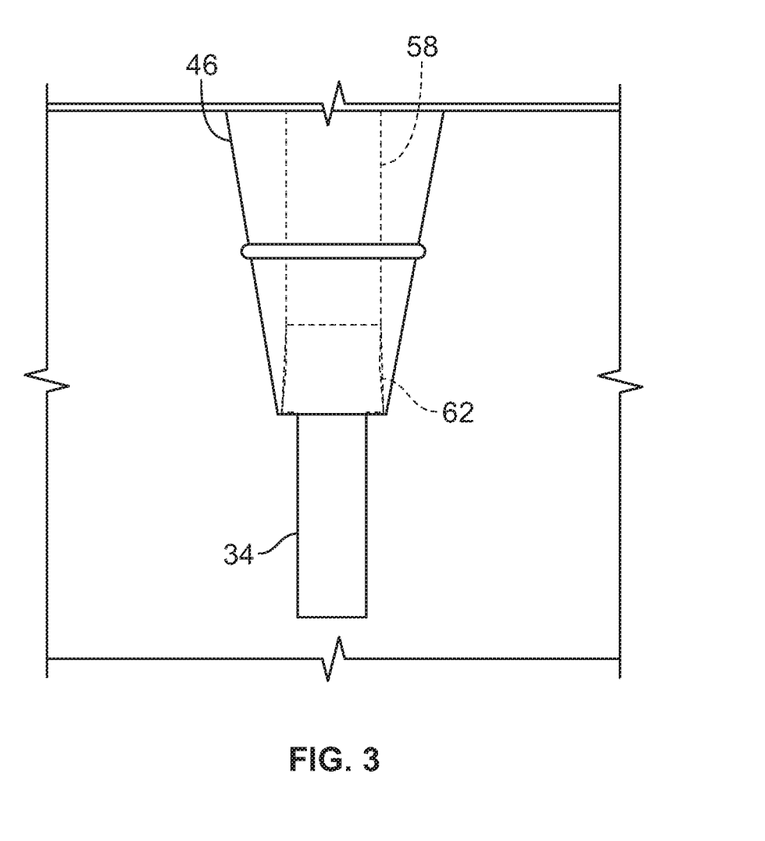
FIG. 3 is an enlarged view of the base portion of interchangeable heads of FIGS. 1 and 2A-2C and the tip of the stem of the adjustable bowel treatment arm of FIG. 1.

As illustrated in FIG. 3, the base 46 of the head 40 features a central bore so that a socket, indicated in phantom at 58 is formed. The proximal end of the stem 34 is provided with a sleeve 62 of resilient material, such as silicone, rubber or plastic. The sleeve is slightly sized and tapered so as to permit entry into the socket 58 of the head base 46 so that a push-fit connector is formed. Other temporary fastening arrangements, including, but not limited to, a threaded arrangement, may alternatively be used.

As illustrated in FIG. 2A, a stool checker head, indicated in general at 64, includes an insertion portion 66, a circular or disc-shaped shield 68 and a base 74. The base 74 features a socket similar to the base 46 of the stool removal head 40 of FIGS. 1, 2B and 3, and thus may be mounted on the proximal end of the stem 34 of the arm in place of the stool removal head using a push-fit connection. The insertion portion 66 has a porous surface so that it will visibly indicate if the patient's rectum contains feces before or after digital stool removal (such as by using the stool removal head) is performed. The stool checker head 64 may also be used before and after alternative stool removal procedures to check for the presence of stool. The insertion portion 66 may be made of, as an example only, of cotton, paper or any other soft, porous material. The stool checker head 64 is preferably disposable.

As illustrated in FIG. 20, an irrigator head, indicated in general at 76, includes an insertion portion 78, a circular or disc-shaped shield 82 and a base 84. The base 84 features a socket similar to the base 46 of the stool removal head 40 of FIGS. 1, 2B and 3, and thus may be mounted on the proximal end of the stem 34 of the arm in place of the stool removal head and the stool checker head using a push-fit connection.

Figure 2C:
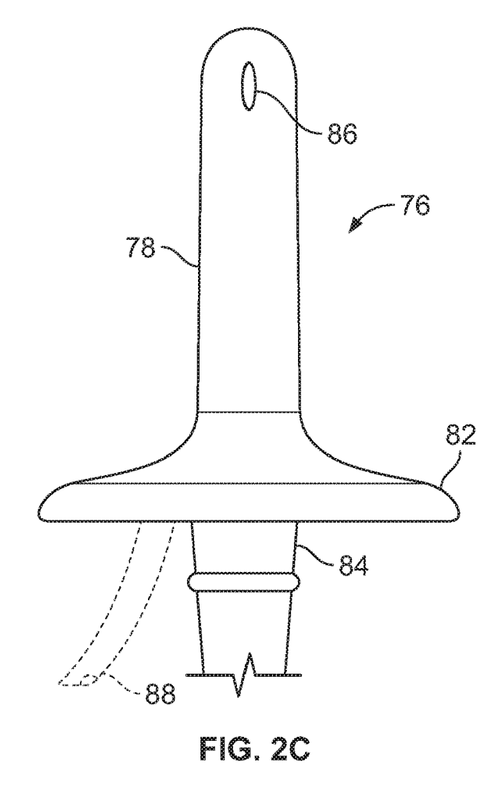

As shown in FIG. 2C, the proximal end of the insertion portion 78 of the irrigator head features one or more irrigation ports 86 which are in fluid communication with a liquid supply line, indicated in phantom at 88, which is attached to a source of pressurized irrigation liquid, such as water. After the insertion portion 78 is positioned within a user's rectum, liquid travels through the supply line 88, through port(s) 86 and into the user's rectum to loosen stool and then flush the stool when the irrigator head is removed from the rectum.

The irrigator head 76 is preferably molded from a soft material, such as silicone (preferably having a durometer of approximately 50 A), acrylonitrile-butadiene-styrene (ABS), thermoplastic elastomer (TPE) or polyurethane. Alternative soft materials may be used.

As alternatives to the heads of FIGS. 2A-20, heads could be used to deliver a medication or a pharma agent to the rectum. As an example only, the head could hold a suppository, or the medication or pharma agent could otherwise be incorporated into the head.

Figure 4:
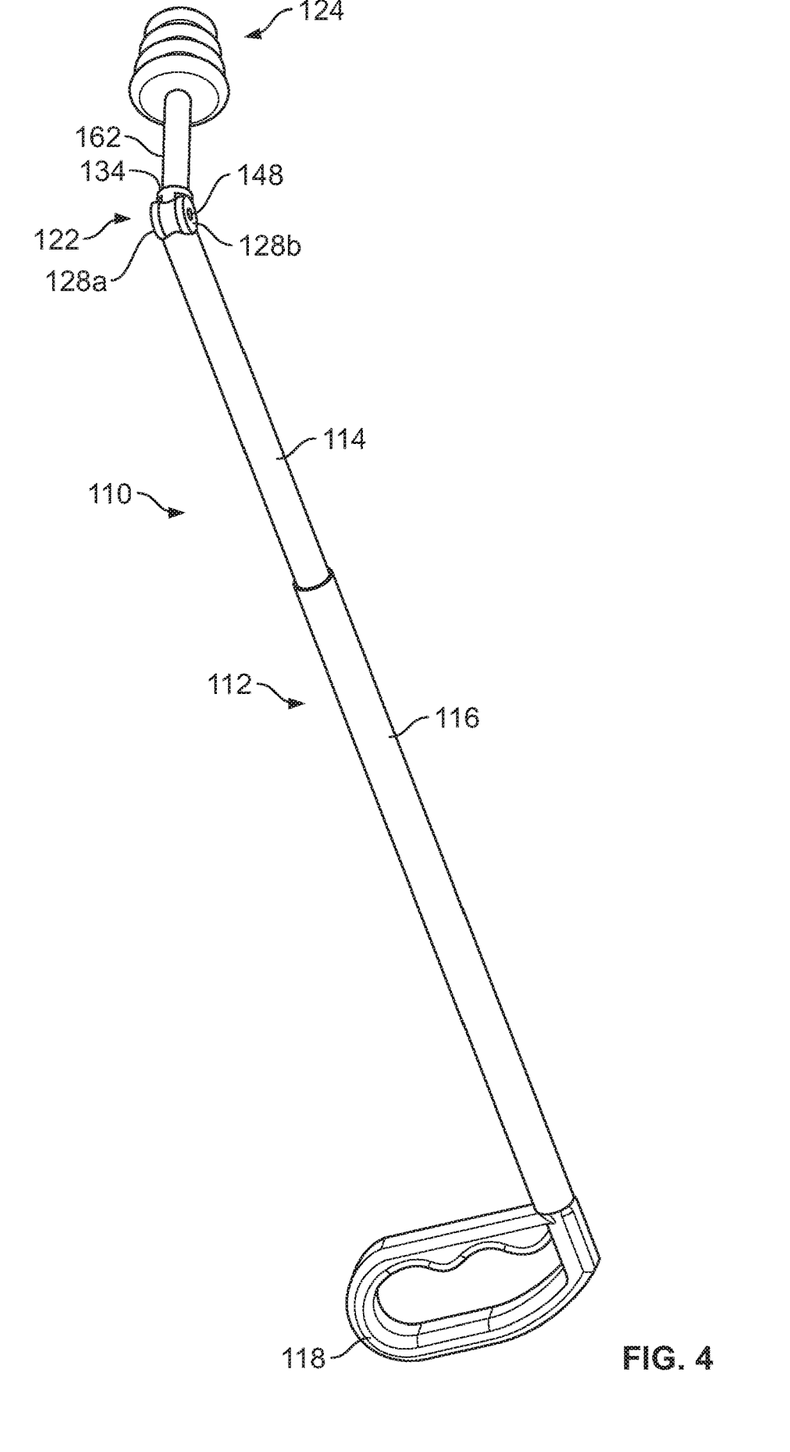
FIG. 4 is a perspective view of a first side of a second embodiment of the adjustable bowel treatment arm of the disclosure.
Figure 5:
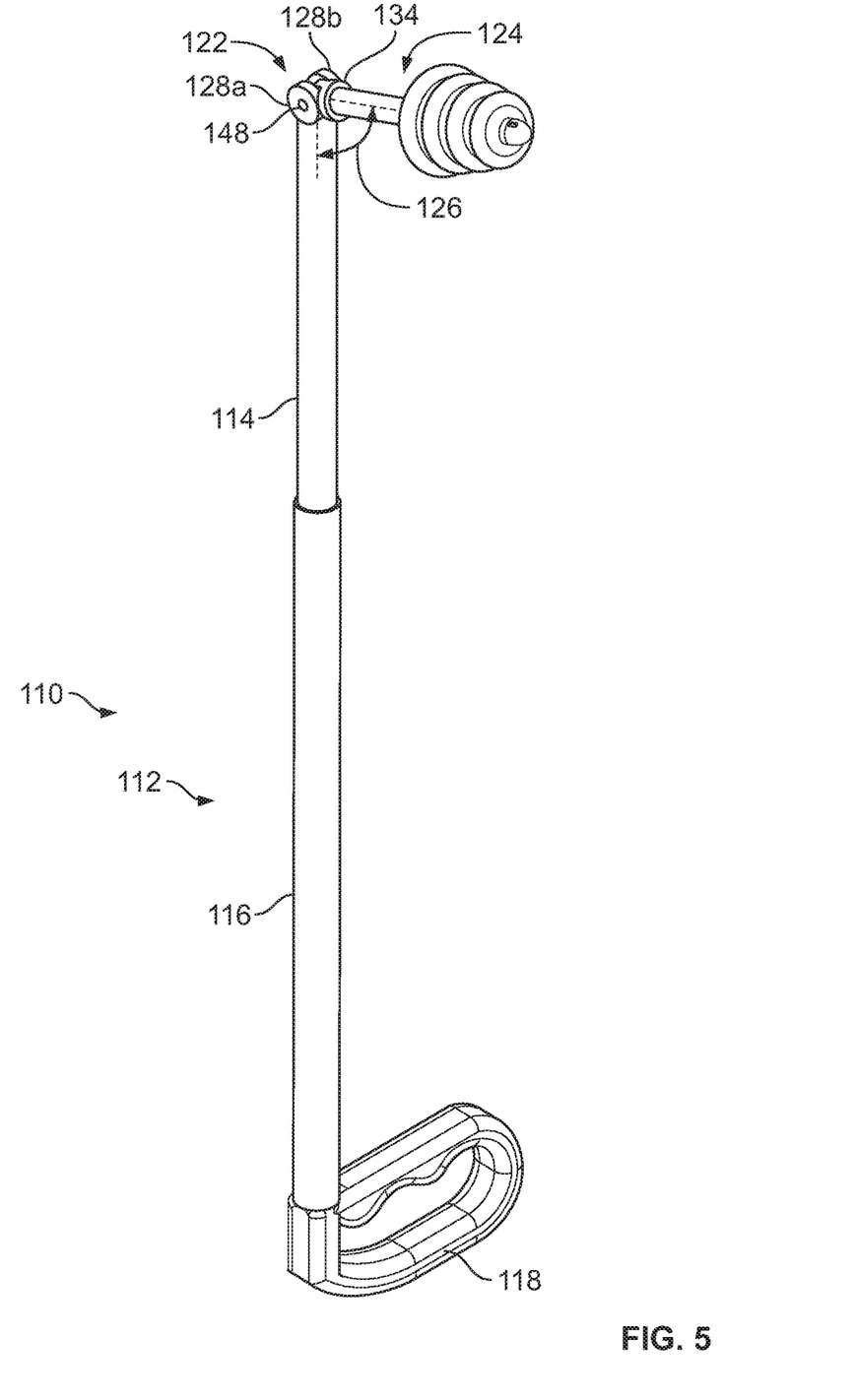
FIG. 5 is a perspective view of a second side of a second embodiment of the adjustable bowel treatment arm of FIG. 4.

A second embodiment of the adjustable bowel treatment arm of the present disclosure is indicated in general at 110 in FIGS. 4 and 5. The adjustable bowel treatment arm features a telescoping shaft, indicated in general at 112, that includes an inner rod 114 and an outer rod 116. The outer rod 116 features a bore that receives the inner rod 114 in a sliding fashion, but with friction between the outer surface of the inner rod 114 and the inner surface of the outer rod 116 so that the selected length is retained. As a result, the length of the telescoping shaft 112 is adjustable. In other embodiments, the selected length of the telescoping shaft may be retained by other mechanisms known in the art including, but not limited to, a spring pin or locking button, a locking collar, a compression fitting or clamp or a flip clamp. Furthermore, in alternative embodiments, the rod 114 could be the outer rod and the rod 116 could be the inner rod.

A D-shaped handle 118 is attached to the distal end of the outer rod 116 and is ergonomically designed to aid the user in inserting a head or attachment positioned on the proximal end of the device into the rectum when the user is on a toilet or lying in a bed.

A pivot junction, indicated in general at 122, is positioned at the proximal end of outer rod 114.

A stool removal attachment, indicated in general at 124, is connected by its distal end to the pivot junction 122 so that the angle of the longitudinal axis of the stool removal attachment with respect to the longitudinal axis of the telescoping shaft, indicated at 126 in FIG. 5, is adjustable.

The inner rod 114 may also be twisted about the longitudinal axis of the telescoping shaft with respect to the outer rod 116 so that the roll angle of the handle about the longitudinal axis of the shaft 112 and the orientation of the handle 118, with respect to the stool removal attachment 124, may also be adjusted. The friction between the outer surface of the inner rod 114 and the inner surface of the outer rod 116 also retains the selected handle orientation.

Figure 6:
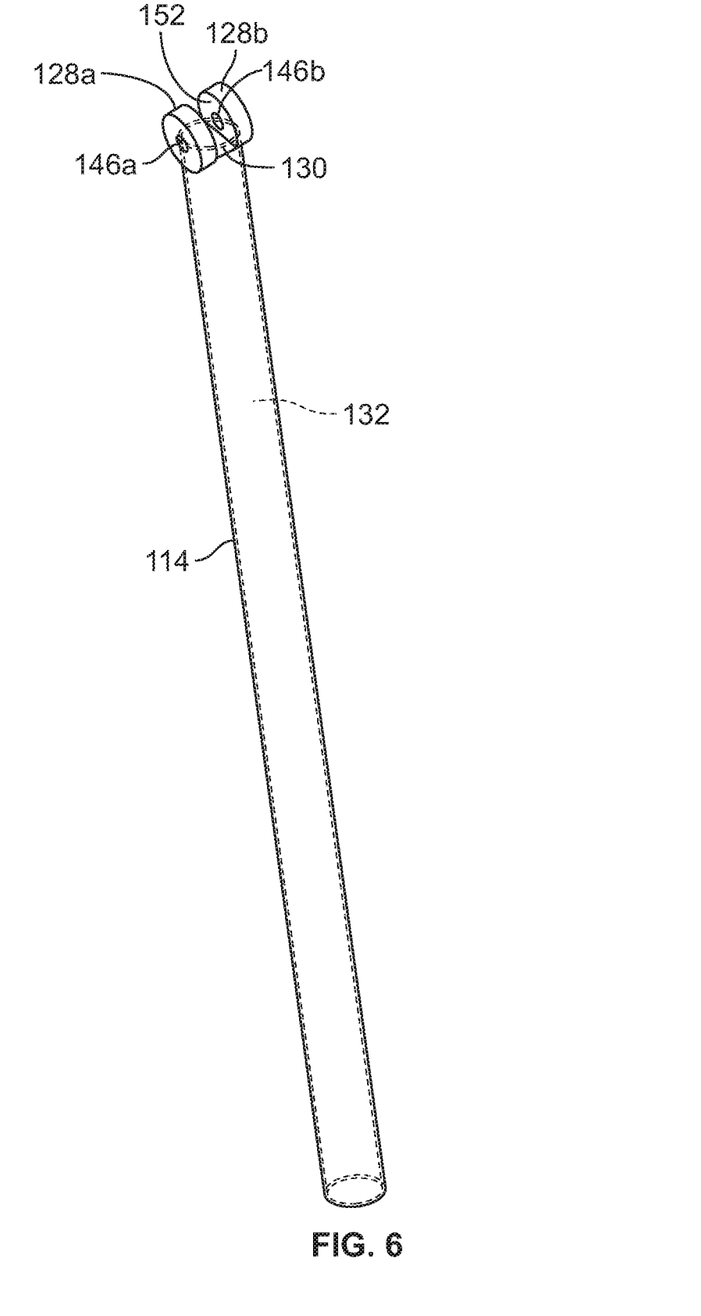
FIG. 6 is an enlarged transparent perspective view of the inner rod of the telescoping shaft of the adjustable bowel treatment arm of FIGS. 4 and 5.

An enlarged perspective view of the inner rod 114 is presented in FIG. 6. A pair of disc-shaped ears or plates 128a and 128b are mounted to the proximal end of the inner rod 114 in a spaced fashion and form a portion of the pivot junction 122 (FIGS. 4 and 5). As an example only, the spaced ears may be molded, along with a base portion 130 that join the two ears, from a single piece of material, such as plastic. The base portion is sized to be received within the proximal end opening of the bore (illustrated in phantom at 132 in FIG. 7) of the inner rod 114 so that the ears 128a and 128b are joined to the proximal end of the inner rod via an interference fit and/or the use of adhesive or other fasteners.

Figure 7:
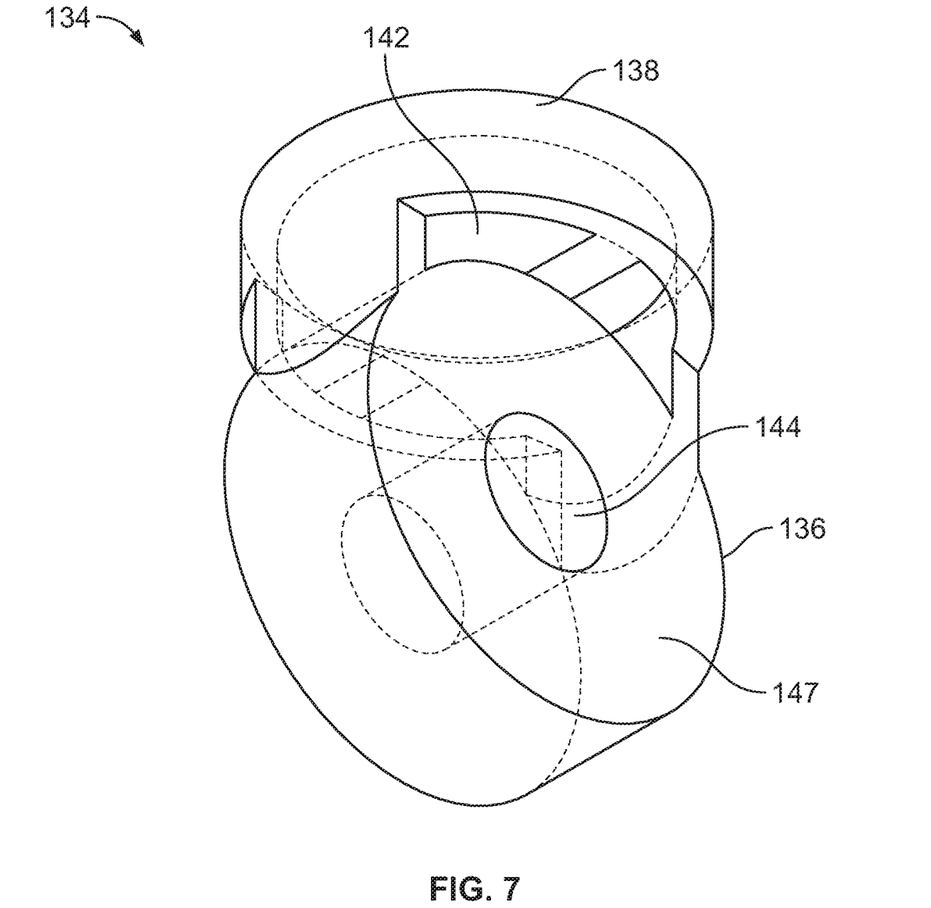
FIG. 7 is an enlarged perspective view of the pivot link of the adjustable bowel treatment arm of FIGS. 4 and 5.

A pivot link, indicated in general at 134 in FIG. 7, forms the remaining portion of the pivot junction. The pivot link 134 includes a disc-shaped pivot plate 136 to which is attached a truncated cylindrical portion 138 which defines a stem-receiving recess 142. The pivot plate 136 is sized to be positioned between the ears 128a and 128b of FIG. 6. As shown in FIG. 7, the pivot plate 136 features a bore 144, and corresponding bores 146a and 146b (FIGS. 4 and 5) are formed in ears 128a and 128b.

As shown in FIGS. 4 and 5, a pin 148 or other fastener passes through the bores of the pivot plate 136 and the ears 128a and 128b to pivotally secure the components together. A friction enhancing material is secured to the outer surfaces (147 of FIG. 7) of the pivot plate 136 and/or the inward facing surfaces of the ears 128a and 128b (152 of FIG. 6) so that the pivoted position of the pivot link with respect to the inner rod is maintained. Alternatively, a friction enhancing surface or formations (such as radial ridges or grooves or knurling) may be formed on pivot link surfaces (147 of FIG. 7) and/or ear inward facing surfaces 152 (FIG. 6).

Figure 8:
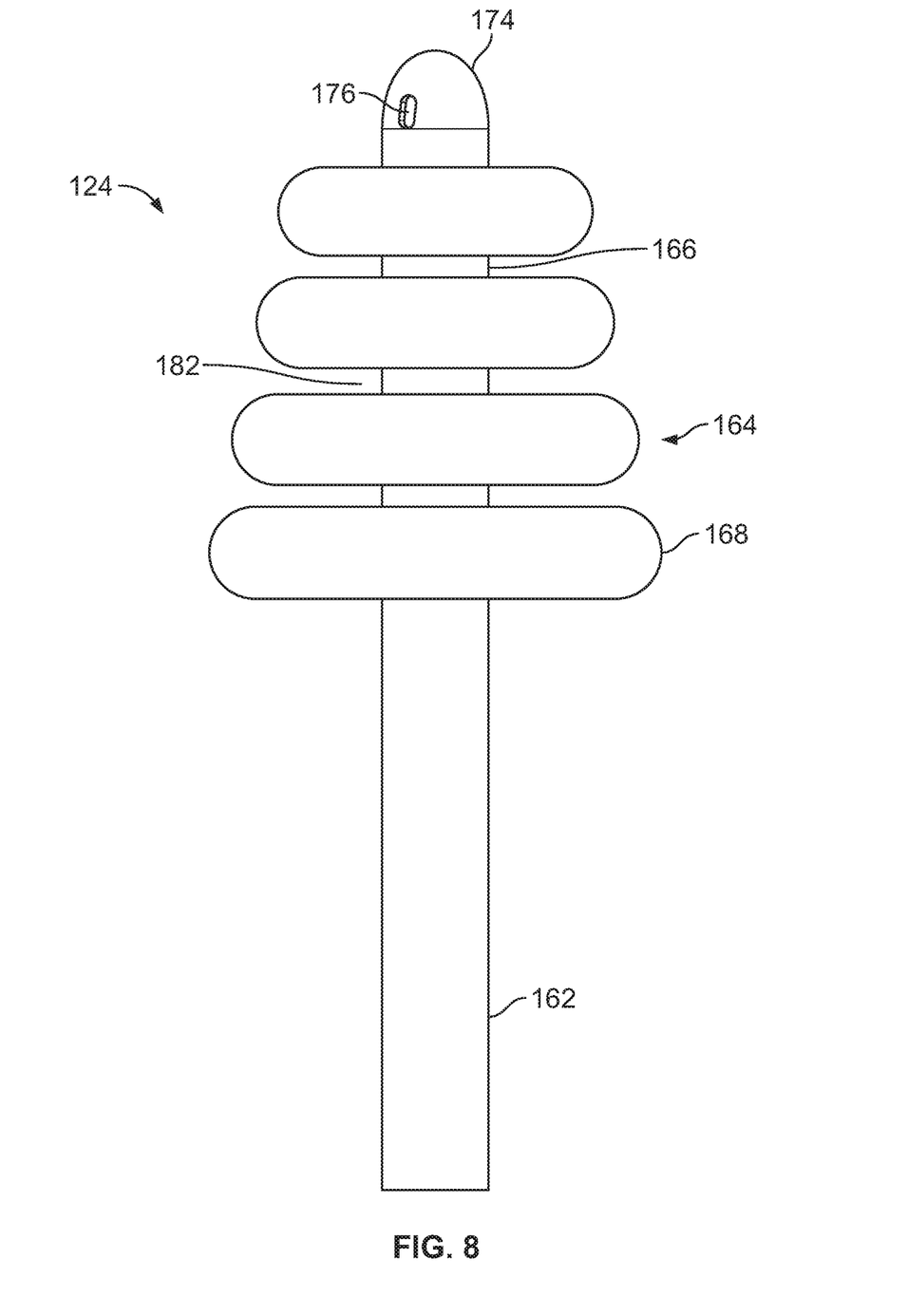
FIG. 8 is an enlarged side elevational view of the stool removal attachment of FIGS. 4 and 5.
Figure 9:
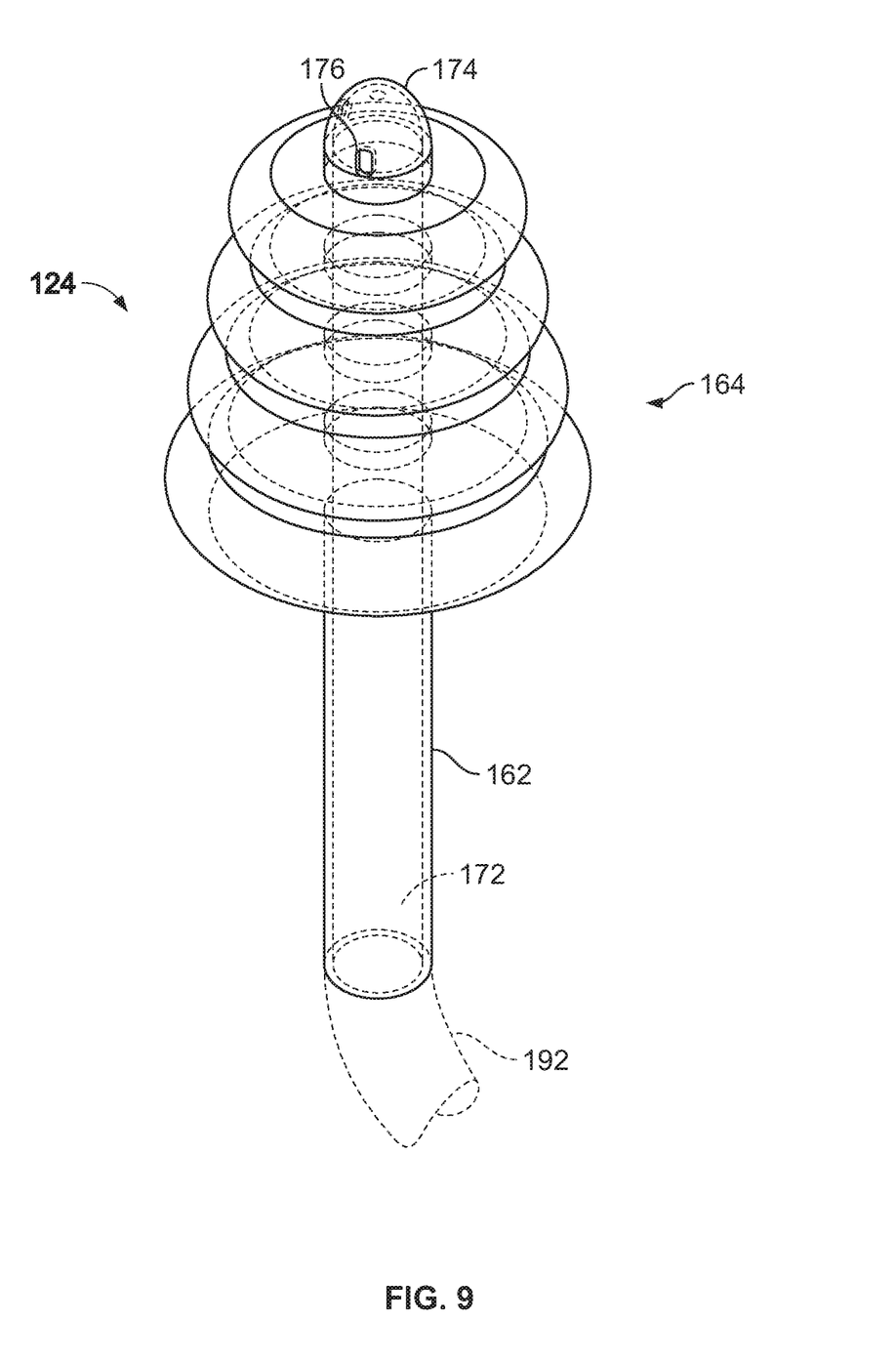
FIG. 9 is transparent perspective view of the stool removal attachment of FIG. 8.

Enlarged views of the stool removal attachment 124 of FIGS. 4 and 5 are presented in FIGS. 8 and 9. The stool removal attachment 124 includes a stem portion 162 and a head, indicated in general at 164. The head includes a central post 166 upon which are concentrically mounted resilient rings 168. As is apparent from FIGS. 8 and 9, the rings 168 decrease in diameter in the direction of travel towards the proximal end of the central post 166.

As illustrated in FIGS. 4 and 5, the distal end of the stem portion 162 engages the stem-receiving recess 142 (FIG. 6) of the pivot link to form a push-fit connection so that the stool removal attachment may be replaced with other attachments (such as stool checker or irrigator attachments). Alternatively, the distal end of the stem portion 162 may be secured within the stem-receiving recess of the pivot link with adhesive (to form a permanent connection), threads or other fastening arrangements (both permanent and temporary) known in the art.

The stem portion 162 and central post 166 of the head of the stool removal attachment are formed from a single tube which, as illustrated in phantom in FIG. 9, includes a central passage 172. The distal end of the tube/stem portion 162 is open while the proximal end of the tube/central post 166 is provided with a cap 174 having one or more irrigation ports 176. As shown in FIG. 9, the cap openings 176 are in fluid communication with the central passage 172 of the post so that when a pressurized irrigation liquid, such as water, is introduced into the distal end opening of the tube/stem 162, the liquid flows out of the irrigation ports 176.

The rings 168 of the stool removal attachment are preferably molded from a high durometer (as an example only, >50 A) silicone-like resilient material so that it is atraumatic to the anal sphincter and rectum. Alternative resilient materials, such as rubber and plastic, may also be used. The tube forming the stem portion 162 and central post 166 of the stool removal attachment is preferably molded from silicone (preferably having a durometer of approximately 50 A), acrylonitrile-butadiene-styrene (ABS), thermoplastic elastomer (TPE) or polyurethane. Alternative materials may be used. The rings 168 may be secured to the central post 166 with adhesive or other fastening arrangements known in the art, or the stem portion 162, central post 166 and rings 168 may be integrally molded as a single piece.

In use, with reference to FIGS. 4 and 5, a user, after the length of the shaft 112, the angle 126 and the roll angle or orientation of the handle about the longitudinal axis of the shaft 112 is adjusted, grasps the handle 118, positions the shaft 112 between his or her legs, under the legs from the side or otherwise approaches from the side, and positions the stool removal attachment 124 at the anus. If the user is sitting on a toilet, the shaft 112 may be rested on the toilet seat or rim of the toilet in a lever arrangement. The user then manipulates the arm to insert the head of the stool removal attachment into his or her rectum.

The concentric rings 168 deflect or collapse during insertion into the user's rectum, which is facilitated by the decrease in ring diameter in the direction of travel towards the proximal end of the stool removal attachment. As a result, once inserted into the rectum, the circumferential edges of the rings 168 gently engage the rectum wall. Stool is collected within the annular spaces 182 (FIG. 8) between the rings and held in place by the rings as the attachment is withdrawn from the user's rectum.

With reference to FIGS. 8 and 9, a tube connected to a source of pressurized irrigation (illustrated in phantom at 192 in FIG. 9) liquid may be attached to the distal open end of the stem 162 in some embodiments so that the stool removal attachment 124 serves as an irrigator head. This may be done either while the stool removal attachment 124 is secured to the pivot link 134 of FIGS. 4 and 5 (in an alternative embodiment) or after it is removed from the pivot link. When the head 164 is positioned within the user's rectum, pressurized liquid is introduced into the central passage 172 of the stem and central post so that liquid flows out of the irrigation ports 176 of the top cap 174 and into the user's rectum. This loosens stool and then flushes the stool when the irrigator head is removed from the rectum. In another embodiment, a second pivot junction, as illustrated in phantom at 194 in FIG. 1, may be added to the stem, or at another location along the arm, to provide additional adjustability.

Figure 10:
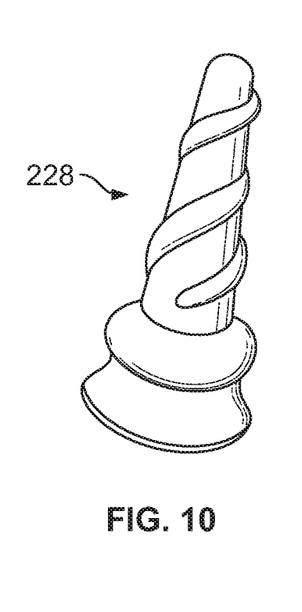
FIG. 10 is a perspective view of a rotational auger head.
Figure 11:
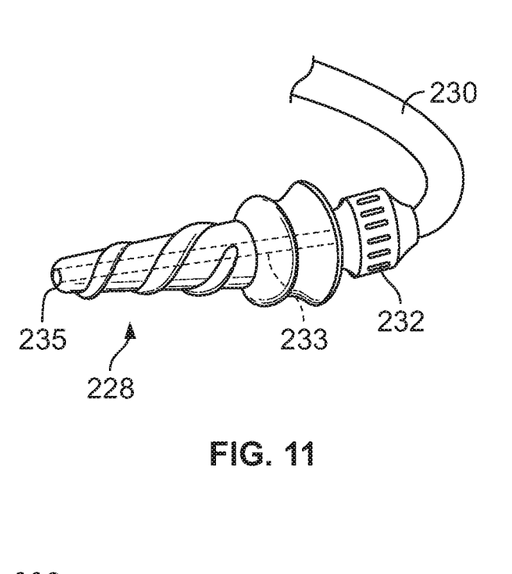
FIG. 11 is a perspective view of the rotational auger head of FIG. 10 attached to an irrigation fluid supply tube.

Turning now to FIGS. 10 and 11, another head or attachment for use with the adjustable bowel treatment arm of the present disclosure is shown. This head provides local digital stimulation of the rectum for the user to promote bowel movement. More specifically, the head is a mechanical device that rotates a shaped stimulation auger, indicated in general 228. The auger is constructed from a flexible material, such as rubber or plastic, and defines a hollow cavity that contains a gel. The head removes stool using a rotating "drill" or "auger" action to both pull stool out of the bowel and provide stimulation. The auger 228 is rotatably mounted to a housing 232, which encloses a motor (not shown) for rotating the auger 228 with respect to the housing. The housing 232 may be attached to the proximal end of either embodiment of the adjustable bowel treatment arm described above.

As shown in FIG. 11, the device may be combined with irrigation to improve the process through a combination of irrigation and stimulation. An irrigation fluid supply tube 230 joins the auger 228 via a passage through housing 232. An irrigation fluid pipe, illustrated in phantom at 233 in FIG. 11, is positioned within the auger 228 and is in fluid communication with irrigation supply tube 230. As a result, irrigation fluid passes out of the auger through an opening 235 (FIG. 11) formed in the auger tip.

Figure 12:
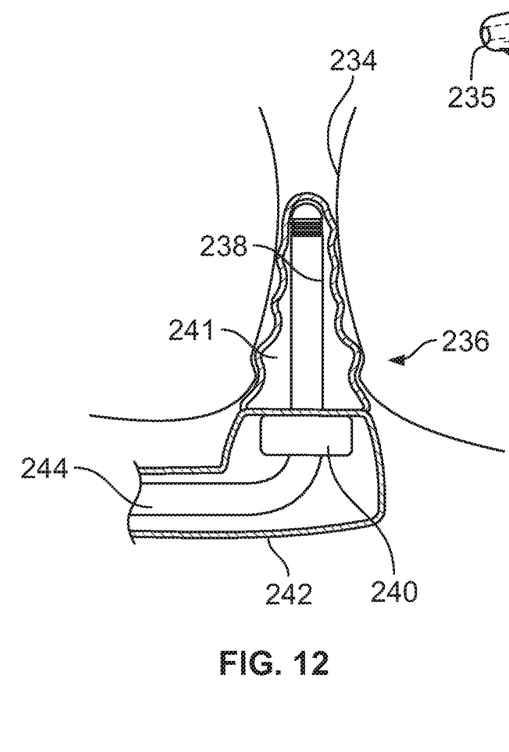
FIG. 12 is a diagrammatic view of the auger head of FIG. 11 inserted in a rectum.

An alternate embodiment of the auger head is indicated in general at 236 in FIG. 12, and shows the auger inserted in a rectum 234. This version has an internal irrigation fluid pipe 238 joined to housing 240. The space 241 surrounding the pipe 238 is filled with gel. The housing 240 also serves as a connector and is positioned inside a proximal end portion 242 of an embodiment of the adjustable arm. The connector 240 receives an irrigation fluid supply tube 244 which also runs through the proximal end portion 242 of the adjustable arm.

The auger heads of FIGS. 10-12 can be used to evacuate hard compact stool in a user's rectum due to the improved design of its cone-shaped auger. The shaped design of the auger will dislodge and break up impacted stool present in the opening of the rectum.

The auger could feature pores so that gel contained therein could flow to the surface of the auger to make the device self-lubricating. Multiple shaped augers could be designed to provide alternative stimulation methods and stool break up options. As mentioned above, one could combine the device with irrigation options during situations where hard stool needs to be removed and dislodged in the rectum prior to irrigation.

Figure 13:
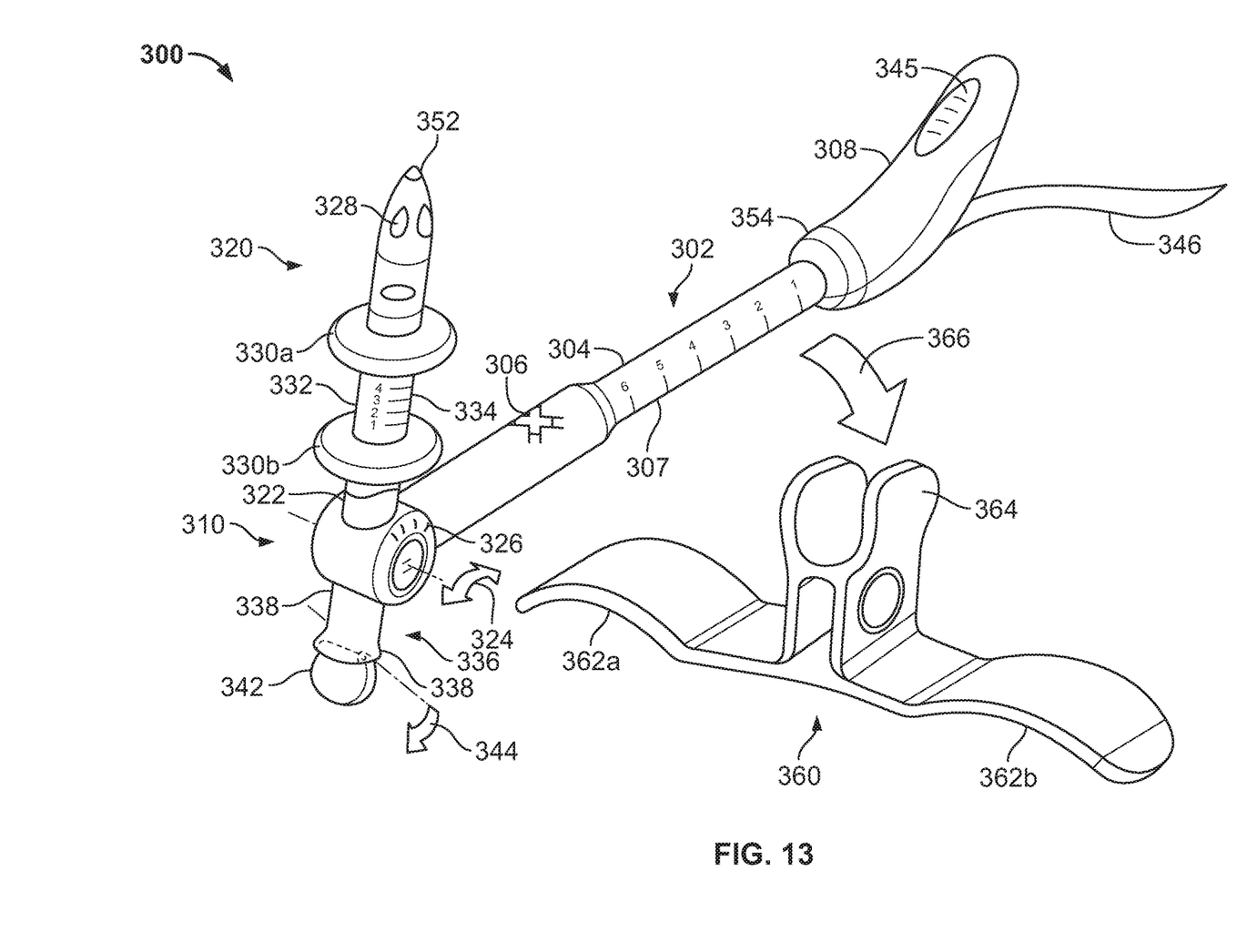
FIG. 13 is a perspective view of a third embodiment of the adjustable bowel treatment arm of the disclosure.

A third embodiment of the adjustable bowel treatment arm of the present disclosure is indicated in general at 300 in FIG. 13. The adjustable bowel treatment arm features a telescoping shaft, indicated in genera a 302, that includes an inner rod 304 and an outer rod 306. The outer rod 306 features a bore that receives the inner rod 304 in a sliding fashion, but with friction between the outer surface of the inner rod 304 and the inner surface of the outer rod 306 so that the selected length is retained. As a result, the length of the telescoping shaft 302 is adjustable. In other embodiments, the selected length of the telescoping shaft may be retained by other mechanisms known in the art including, but not limited to, a spring pin or locking button, a locking collar, a compression fitting or clamp or a flip clamp. The inner rod 304 features markings 307 to indicate the positioning of the inner rod relative to the outer rod.

A handle 308 is attached to the distal end of the inner rod 304, while a pivot junction, indicated in general at 310 in FIG. 13, is positioned at the proximal end of the outer rod 306. In an alternative embodiment, the positions of the inner and outer rods could be reversed so that the handle is attached to the distal end of the outer rod and the pivot junction is positioned at the proximal end of the inner rod.

An irrigation head, indicated in general at 320, has a bottom end received within a socket 322 of the pivot junction 310. The irrigation head 320 is preferably disposable and removably attached to the pivot junction. Alternative attachment arrangements known in the art may be used to join the irrigation head 320 to the pivot junction 310 either in a removable or non-removable fashion.

As indicated by arrow 324, the angle of the longitudinal axis of the irrigation head 320 may be adjusted with respect to the longitudinal axis of the telescoping shaft 302. The pivot junction 310 may be provided with markings 326 to indicate the selected angle.

The inner rod 304 may also be twisted about the longitudinal axis of the telescoping shaft with respect to the outer rod 306 so that the roll angle of the handle 308 about the longitudinal axis of the shaft 302 and the orientation of the handle 308, with respect to the irrigation head 320, may also be adjusted. The friction between the outer surface of the inner rod 304 and the inner surface of the outer rod 306 also retains the selected handle orientation.

The irrigation head 320 features a tubular construction so that a central passage is defined that is in fluid communication with irrigation openings 328 formed in the tapered tip portion of the irrigation head.

The irrigation head includes a pair of annular shields 330*a* and 330*b*. The shields 330*a* and 330*b* are separated by a transanal portion 332 and preferably molded from a high durometer (as an example only, >50 A) silicone-like resilient material so that they are atraumatic to the anal sphincter and rectum. Alternative resilient materials, such as rubber and plastic, may be used. In use, the shield 330*a* is inserted through the anus and into the rectum, while the shield 330*b* remains outside of the rectum. The transanal portion 332 may be provided with markings 334 to assist a user in assuring that the irrigation head 320 is properly positioned within the rectum.

The pivot junction 310 is provided with a flushing valve, indicated in general at 336. The flushing valve includes a skirt portion 338 that defines a flushing passage having a top opening that is in fluid communication with the central passage of the irrigation head 320 and a bottom opening 338. A flushing valve cover 342 is pivotally attached to the skirt portion 338 of the flushing valve. As a result, the flushing valve cover 342 may be used to cover the bottom opening 338 and then pivoted, as indicated by arrow 344, to open the valve so that the contents (including irrigation liquid and fecal matter) within the central passage of the irrigation head 320 may be drained into a toilet, bedpan or the like. The latch to retain the flushing valve cover 342 in the closed position may be released by a button 345 positioned on the handle 308 (using linkage arrangements known in the art).

An irrigation line 346 is attached to a source of irrigation liquid, passes through the telescoping shaft 302 and is in fluid communication with central passage of the irrigation head 320. Alternatively, telescoping shaft 302 may include a central passage that is in fluid communication with the irrigation line 346 and the central passage of the irrigation head 320 so that the irrigation line 346 does not extend through the telescoping shaft 302.

A temperature sensor, illustrated at 352 in FIG. 13, may optionally be positioned within the tip of the irrigation head 320 and a microcontroller may receive a temperature signal from the sensor. The microprocessor may be programmed to illuminate an "on target" indicator light 354 positioned on or in the handle 308 when the tip of the irrigation head is properly positioned at a user's anus, as detected by a corresponding rise in temperature. An as example only, the microprocessor could be positioned within the handle 308.

In use, after the irrigation head is inserted into the user's rectum, irrigation liquid is introduced into the rectum via the openings 328 of the irrigation head 320. The user may then flush the irrigation liquid and fecal matter from rectum and the irrigation head 320 by pressing the button 345 (on the handle 308) to open the flushing valve 336, that is, release the cover 342 so that it pivots into the position shown in FIG. 13. The user may then withdraw the irrigation head 320 from the rectum, disconnect it from the arm and properly dispose of it.

A lateral support, indicated in general at 360 in FIG. 13, is optionally provided. The lateral support 360 includes a pair of wings 362a and 362b that include curved portions to rest on top of a user's thighs. A central portion includes a clamp 364 that, as illustrated by arrow 366, receives the telescoping shaft 302 of the adjustable bowel treatment arm 300 in a snap-fit fashion. In a preferred embodiment (shown), the clamp 364 is a U-shaped structure made of a resilient material, such as plastic. Alternative clamping structures known in the art may be used in place of the U-shaped structure shown in FIG. 13.

When the lateral support 360 is attached to the arm 300 of FIG. 13, the user may rest the wings 362a and 362b on the tops of his or her thighs to provide a fulcrum and facilitate steady guidance of the irrigation head 320.

In an alternative embodiment, the wings of the lateral support may be pivotally attached to opposite sides of the outer rod 306 of the telescoping shaft 302. In such an embodiment, the lateral support is integrated into the adjustable bowel treatment arm itself, and the wings may be folded against the telescoping shaft for ease of storage and transport.

The embodiments of the disclosure therefore replace manual evacuation and thus remove the need for users to utilize their fingers by providing a discreet and adjustable hand-held stool evacuation device that is easy to use. The embodiments may be utilized on their own or in conjunction with other bowel treatment methods (such as trans-anal irrigation) to check if there stool remaining in the rectum after treatment.

While the preferred embodiments of the disclosure have been shown and described, it will be apparent to those skilled in the art that changes and modifications may be made therein without departing from the spirit of the disclosure, the scope of which is defined by the appended claims.

What is claimed is:

1. An adjustable bowel treatment arm comprising:
   a. a telescoping shaft having a proximal end and a distal end;
   b. a handle secured to the distal end of the telescoping shaft;
   c. a pivot junction positioned at the proximal end of the telescoping shaft;
   d. a stem having a proximal end and a distal end, where the distal end of the stem is attached to the pivot junction; and
   e. a head attached to the proximal end of the stem; and
   f. a lateral support including a pair of wings adapted to support the telescoping shaft on a user's legs.

2. The adjustable bowel treatment arm of claim 1 wherein the head is detachable from the proximal end of the stem.

3. The adjustable bowel treatment arm of claim 1 wherein the pivot junction includes a spaced pair of ears positioned upon the proximal end of the telescoping shaft and a pivot link attached to the distal end of the stem with the pivot link pivotally secured between the pair of ears.

4. The adjustable bowel treatment arm of claim 1 wherein the stem and head form an attachment and the distal end of the stem may be detached from the pivot junction.

5. The adjustable bowel treatment arm of claim 4 wherein the pivot junction includes a spaced pair of ears positioned upon the proximal end of the telescoping shaft and a pivot link attached to the distal end of the stem with the pivot link pivotally secured between the pair of ears and the distal end of the stem detachably connected to the pivot link.

6. The adjustable bowel treatment arm of claim 1 wherein the head includes a stool checker including a porous material.

7. The adjustable bowel treatment arm of claim 1 wherein the head includes a plurality of fins or rings including a resilient material.

8. The adjustable bowel treatment arm of claim 1 wherein the head includes an irrigation port adapted to be place in fluid communication with a source of pressurized irrigation fluid.

9. The adjustable bowel treatment arm of claim 1 wherein the head includes an auger.

10. The adjustable bowel treatment arm of claim 9 wherein the head includes a motor adapted to rotate the auger.

11. The adjustable bowel treatment arm of claim 9 wherein the auger contains a gel.

12. The adjustable bowel treatment arm of claim 9 wherein the head includes a tube having a central passage and an irrigation port, with the central passage in fluid communication with the irrigation port and adapted to be place in fluid communication with a source of pressurized irrigation fluid.

13. The adjustable bowel treatment arm of claim 1 wherein the head includes a medication or a pharma agent.

14. The adjustable bowel treatment arm of claim 1 wherein the lateral support is removably attached to the telescoping shaft.

15. The adjustable bowel treatment arm of claim 1 wherein the pair of wings of the lateral support are pivotally attached to the telescoping shaft.

* * * * *